United States Patent
Williams et al.

(10) Patent No.: US 6,210,319 B1
(45) Date of Patent: Apr. 3, 2001

(54) INTRA-AORTIC BALLOON PUMP CONDENSATION PREVENTION SYSTEM

(75) Inventors: Jonathan Williams, Montville; Robert Hoff, Cedar Grove; Yefim Kaushansky, Fairlawn, all of NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/296,063

(22) Filed: Apr. 21, 1999

(51) Int. Cl.[7] ................................................ A61B 19/00
(52) U.S. Cl. ................................................................ 600/18
(58) Field of Search ............................ 600/16–18; 623/3

(56) References Cited

U.S. PATENT DOCUMENTS

| | | | |
|---|---|---|---|
| 5,042,500 | * | 8/1991 | Norlien et al. ........................ 128/719 |
| 5,045,051 | * | 9/1991 | Milder et al. ........................... 600/16 |
| 5,421,807 | * | 6/1995 | Atsumi .................................. 600/16 |
| 6,082,105 | * | 7/2000 | Miyata .................................. 60/410 |

* cited by examiner

Primary Examiner—Jeffrey R. Jastrzab
(74) Attorney, Agent, or Firm—Abraham Ronai

(57) ABSTRACT

An intra-aortic balloon pump condensation prevention system comprising a water vapor extracting element. In one embodiment, the water vapor extracting element may comprise a Nafion tube. Said Nafion tube absorbs water vapor in the intra-aortic balloon catheter shuttle gas. The water is then extracted from the Nafion tube by means of a vacuum supply or a dry purge gas. In another embodiment, the water vapor extracting element may comprise a cooled coiled section of tubing. Water vapor which condenses in said coiled section of tubing migrates towards a sump as a result of the intermittent one-way flow of shuttle gas through the water vapor extraction element.

10 Claims, 4 Drawing Sheets

INTRA-AORTIC BALLOON PUMP CONDENSATION PREVENTION SYSTEM

BACKGROUND OF THE INVENTION

1. Field of the Invention

The invention relates to an intra-aortic balloon pump condensation prevention system. More particularly, the invention relates to an improved system for preventing water vapor from condensing in the shuttle gas of an intra-aortic balloon pump system.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body. A passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heart beat.

Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon. Helium gas is typically used as the "shuttle gas", the gas used to inflate and deflate the IAB. To be effective, the IAB inflation and deflation must occur rapidly, e.g. in less than one eighth of a second.

During operation of the IAB helium gas diffuses from the IAB to the patient and the atmosphere and water vapor diffuses from the patient into the IAB. The outer tube of the IAB is thin (approximately 0.004 inches thick) and is generally made from a mixture of polyurethane and silicone, materials permeable to helium and water vapor, and thus allows for the above mentioned diffusion. To compensate for the foregoing loss of helium, intra-aortic balloon pumping (IABP) systems replace or add helium gas on a periodic basis. If the helium is not replaced on a periodic basis then the balloon will not completely inflate and therapy can be diminished. If the helium is not replaced at all the balloon will simply not inflate.

To compensate for the introduction of water vapor into IABP system some IABP systems incorporate a water vapor removal device which removes or lowers the concentration of water vapor in the IAB's shuttle gas. If the concentration of the water vapor is not lowered, the water vapor will condense and appear as liquid water within the IABP's shuttle gas system. Over a sufficient period of time the water can accumulate and impede the flow of shuttle gas within the IABP system.

Condensation can be prevented if the dew point temperature of the shuttle gas is kept lower than the IABP's ambient temperature. Prior art IABP systems prevent condensate accumulation by using a thermo-electric cooler, such as a Peltier device. The cooler is used to keep a metallic block (a condensate trap) colder than IABP ambient temperatures. During IABP operation, the shuttle gas (helium) flows thru a drilling in the block. Due to the block's lower temperature condensate forms within the block and flows (due to force of gravity) into a sump. Periodically, the sump is automatically emptied via a valve. Shuttle gas is lost during the emptying process. Consequently, the sump is emptied concurrently with the shuttle gas removal or replacement.

The prior art condensate prevention systems have a number of drawbacks. First, emptying the sump causes a loss of shuttle gas, and therefore, the helium consumption of the prior art condensation prevention systems is higher. Furthermore, because the sump cannot be emptied without a loss of shuttle gas, emptying the sump requires a shutdown of the IABP system, and therefore, causes an interruption in therapy. Second, the thermoelectric cooler consumes a great deal of power cooling the condensate trap (the block), which is continuously warmed by the flow of shuttle gas. High power consumption is undesirable because a larger IABP system power supply, battery charger, and battery is required to accommodate such consumption. Third, the drillings within the condensate trap increase the dead volume within the shuttle gas system. During balloon inflation and deflation the velocity of the shuttle gas is very high. To maintain high IAB inflate/deflate speeds it is important to prevent unnecessary pressure drops in the shuttle gas circuit. To accommodate this design requirement the drillings within the condensate trap are made quite large. Unfortunately, the large drillings increase the dead volume in the shuttle gas system. Parasitic dead volume wastes IABP power and can reduce efficacy by-increasing the pneumatic compliance of the shuttle gas system. Fourth, the prior art systems require disassembly and replacement or sterilization of the condensate trap if blood enters the IAB. Occasionally, arterial plaque deposits abrade the IAB's membrane and thereby cause perforations in the membrane. When this occurs, blood can enter the IAB and may contaminate components within the shuttle gas system. In prior art systems, IAB blood penetration requires disassembly and replacement of the condensate trap. A final drawback of the prior art condensate prevention system is that it is orientation sensitive, i.e. the condensate trap relies on gravity. Orientation sensitivity of a system component limits the design flexibility of the entire IABP system.

The IABP condensate prevention systems discussed above are essentially devices which dry "wet" process gases. Perma-Pure Inc. manufactures a commercially available device for drying a "wet" process gas. Said device is generic, i.e. it is not made specifically for use with a specific machine or system, such as a an IABP system. Wet gas flows through a specially formulated plastic tube, made of Nafion, which is surrounded by a co-axial housing. The housing's interior, the area between the inner surface of the co-axial housing and the outer surface of the Nafion tube, is continuously swept with a dry "purge" gas. The purge gas and the process gases can differ in composition. As the wet process gas flows though the central tubing its water vapor is absorbed by the tubing wall and is transported to the purge gas. If the flow rate of the process gas is sufficiently low it is dried as it exits the assembly's Nafion tubing. A major disadvantage with the Perma-Pure drying system is that it requires a continuous source of dry process gas. A similar dehumidifier system using a membrane cartridge is disclosed in U.S. Pat. No. 5,681,368.

While the prior art designs may be suitable for the particular purpose employed, or for general use, they would not be as suitable for the purposes of the present invention as disclosed hereafter.

SUMMARY OF THE INVENTION

Accordingly, it is an object of the invention to produce an improved IABP condensation prevention system, using Nafion tubing as an agent to reduce the concentration of water vapor in the shuttle gas to levels which prevent condensation from forming, which overcomes the numerous above mentioned drawbacks of the prior art condensation prevention systems.

It is another object of the invention to produce a condensate prevention system which consumes less helium.

It is yet another object of the invention to produce a condensate prevention system which does not require an interruption of therapy to empty a sump.

It is a further object of the invention to produce a condensate prevention system with a considerably lower power consumption.

It is a still further object of the invention to produce a condensate prevention system with minimum parasitic dead volume space and with a dead volume location which has a minimum effect on the inflate and deflate speed of the intra-aortic balloon.

It is still yet another object of the invention to produce a condensate prevention system which does not have to be disassembled and placed if blood enters the IAB.

It is still a further object of the invention to produce a condensate prevention system which is not orientationaly sensitive, i.e. which does not rely on gravity.

The invention is an intra-aortic balloon pump condensation prevention system comprising a water vapor extracting element. In one embodiment, the water vapor extracting element may comprise a Nafion tube. Said Nafion tube absorbs water vapor in the intra-aortic balloon catheter shuttle gas. The water is then extracted from the Nafion tube by means of a vacuum supply or a dry purge gas. In another embodiment, the water vapor extracting element may comprise a cooled coiled section of tubing. Water vapor which condenses in said coiled section of tubing migrates towards a sump.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
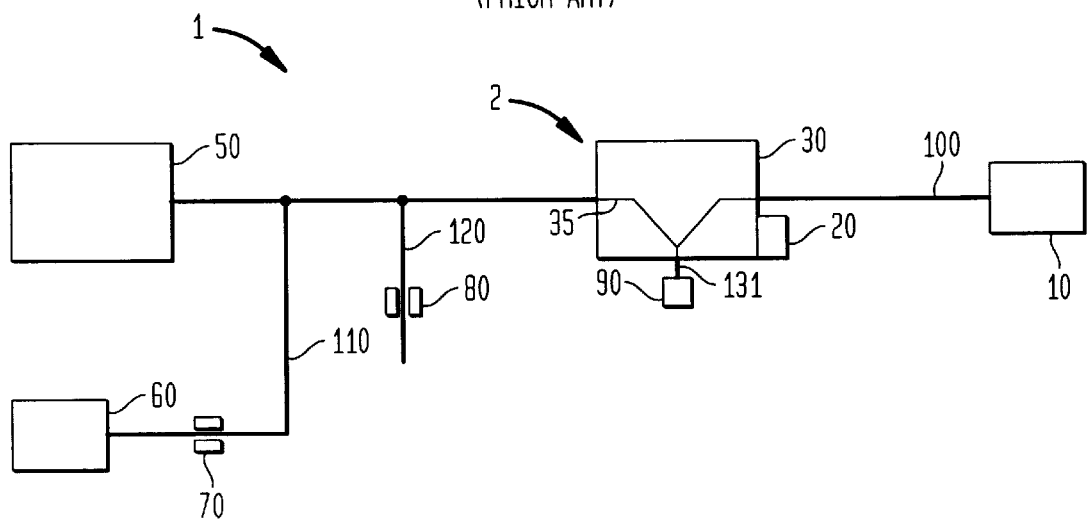
FIG. 1 is a block diagram of an intra-aortic balloon pump system having a prior art condensation prevention system.

FIG. 1 illustrates a block diagram of an intra-aortic balloon pump (IABP) system, generally designated 1, with a prior art condensation prevention system, generally designated 2. The IABP system 1 comprises an intra-aortic balloon (IAB) 10, a catheter 100, a pump 50, the condensation prevention system 2, and a shuttle gas supply 60. The condensation prevention system comprises a cooler 20, a cold trap 30, and a sump 90. The pump 50 and the IAB 10 are connected by the catheter 100. The shuttle gas supply 60 is connected to the catheter 100 by a first line 110. The amount of shuttle gas supplied by the shuttle gas supply 60 is controlled by a shuttle gas supply pinch valve 70. Shuttle gas is added to compensate for shuttle gas losses due to diffusion from the IAB to the patient, as discussed above. Helium is generally used for the shuttle gas. A second line 120 acts as a vent and is controlled by a vent pinch valve 80. The pump 50 shuttles shuttle gas, supplied by the shuttle gas supply 60, back and forth inflating and deflating the IAB 10. As the shuttle gas shuttles back and forth in the catheter 100, between the pump 50 and the IAB 10, the shuttle gas passes through a drilling 35 in the cold trap 30. The cold trap 30 is cooled by the cooler 20. As the shuttle gas is cooled, water vapor, which has diffused from the patient into the shuttle gas in the IABP system 1, condenses in the drilling 35 of the cold trap 30 and trickles down into the sump 90, which communicates with the trap 30 by means of a third line 131. A valve (not shown) is connected to the sump 90 so as to allow for a periodic emptying of the sump 90.

Figure 2:
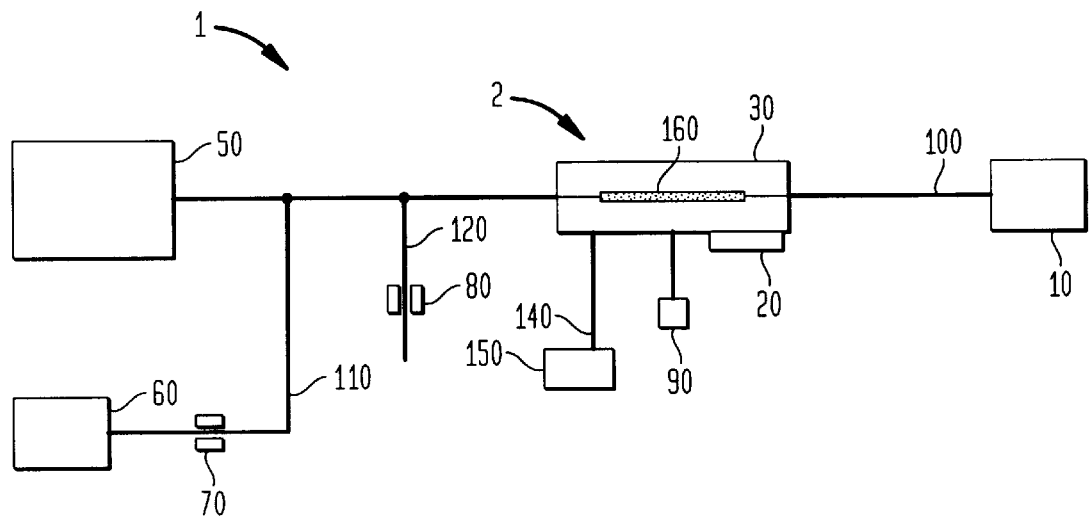
FIG. 2 is block diagram of an intra-aortic balloon pump system with an improved condensation prevention system with a water vapor extraction element in line with the catheter.

FIG. 2 illustrates a block diagram of an IABP system 1 with an improved condensation prevention system, generally designated 2. The improved IABP system 1 (FIG. 2) is physically similar to the prior art IABP system 1 (FIG. 1) except for the change in the condensation prevention system 2, specifically the incorporation of a water vapor extraction element 160 in line with the catheter 100. The water vapor extraction element 160 is preferably a perfluorosulfonate ionomer tube, such as Nafion made by DuPont. The cold trap 30 communicates with a vacuum supply 150, via a fourth line 140, and a sump 90. The cooler 20 is significantly smaller than the cooler 20 (FIG. 1) used in the prior art condensation prevention system because the improved condensation prevention system consumes approximately $\frac{1}{25}$ the power. The prior art cooler 20 consumes 5 Watts as compared to 0.2 Watts consumed by the improved condensation system cooler 20. It should be noted that exposure of the Nafion tube to atmosphere without use of either the housing, cooling, and vacuum is anticipated. However, it is believed that use of these elements increases the water vapor removal efficiency of the system.

As the shuttle gas shuttles back and forth between the pump 50 and the IAB 10, in the catheter 100, the shuttle gas passes through the water extraction element 160 in the cold trap 30. Water vapor in the shuttle gas is absorbed by the water vapor extraction element 160. The vacuum supply 150 maintains a pressure in the cold trap 30 which is lower than the pressure in the catheter 100. The pressure differential between the catheter 100 and the cold trap 30 facilitates the migration of the water vapor from the shuttle gas to the water vapor extraction element 160 into the cold trap 30, and finally, out of said cold trap 30 and into the sump 90.

Most IABP systems use a compressor and aspirator as part of their pneumatic drive. Thus, the vacuum supply 150 is readily available. The cooler 20 is used to chill the Nafion tube 160 in order to increase its water removing efficiency.

Note, however, that use of the improved condensation prevention system without the cooler 20 is anticipated. In an alternate embodiment, the function of the vacuum 150 may be replaced with a dry gas flush. A gas, having a lower water vapor content than the shuttle gas shuttle gas, may be used to flush the water vapor extraction element 160. Said flush gas removes the water vapor from the water vapor extraction element 160. The flush gas may be supplied by a compressor/aspirator (not separately shown, but may be part of the pump 50).

Figure 3:
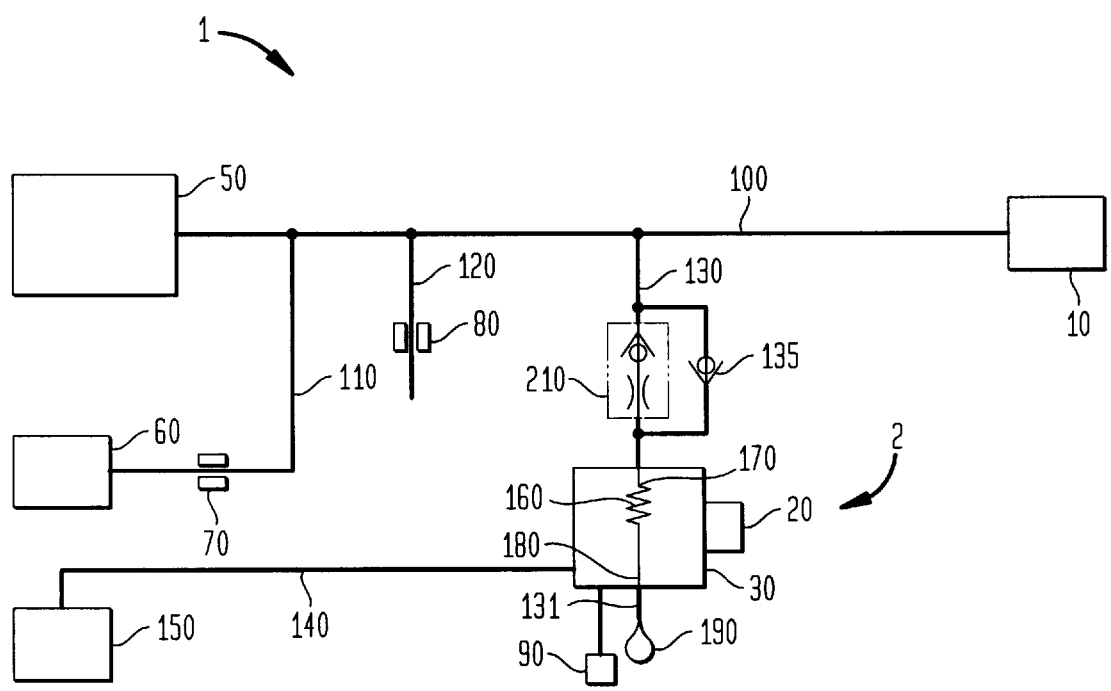
FIG. 3 is a block diagram of an alternate embodiment of the intra-aortic balloon pump system with an improved condensation prevention system.

FIG. 3 illustrates a block diagram of another alternate embodiment of the IABP system 1 with an improved condensation prevention system 2. The cold trap 30 communicates with a vacuum supply 150, via a fourth line 140, and also incorporates a water vapor extraction element 160, preferably a Nafion tube. The water vapor extraction element 160 has a first end 170, which is connected to a third line 130, and a second end 180 which is connected to a tidal balloon 190, or alternatively to a safety disk (see FIGS. 4 and 5). The third line 130 connects the cold trap 30 to the catheter 100. A restricted check valve 210 is connected on the third line 130. A second check valve 135, connected in parallel with restricted check valve 210, acts as a one-way bypass of restricted check valve 210. The cooler 20 is significantly smaller than the cooler 20 (FIG. 1) used in the prior art condensation prevention system 2 (FIG 1)because the improved condensation prevention system 2 consumes approximately ¹⁄₂₅ the power. The prior art cooler 20 consumes 5 Watts as compared to 0.2 Watts consumed by the improved condensation system cooler 20.

As the shuttle gas shuttles back and forth in the catheter 100, between the pump 50 and the IAB 10, some shuttle gas enters the water vapor extraction element 160 in the cold trap 30 via the third line 130. Water vapor in the shuttle gas is absorbed by the water vapor extraction element 160. The vacuum supply 150 maintains a pressure in the cold trap 30 which is lower than or equal to the pressure in the catheter 100. This pressure differential facilitates the migration of water vapor from the shuttle gas to water vapor extraction element 160 into the cold trap 30 and out of said cold trap 30 and into the sump 90. If Nafion is used for the water vapor extraction element 160, the pressure differential created by the vacuum supply 150 also prevents the collapse of the water vapor extraction element 160 due to the pressure gradient across its walls. The sump 90 is periodically emptied of water by means of a valve (not shown).

As discussed above, most IABP systems use a compressor and aspirator as part of their pneumatic drive. Thus, the vacuum supply 150 is readily available. The cooler 20 is used to chill the water vapor extraction element 160 in order to increase its water removing efficiency. Note, however, that use of the improved condensation prevention system without the cooler 20 is anticipated. Note further, the vacuum 150 may be replaced by a system which purges the water vapor extraction element 160 with a dry purge gas, i.e a purge gas having a lower water vapor level than the shuttle gas shuttle gas.

The improved condensate prevention system 2 operates in the following manner. During normal operation of the IABP system 1, the pressure at the junction between the first line 100 and the third line 130 rises and falls as a consequence of the pumping action of the pump 50. In response to these pressure swings, the tidal balloon 190 inflates. If the safety disk 190 is used, it moves from a low volume position, as illustrated in FIG. 4, to a high volume position, as illustrated in FIG. 5.

Figure 4:
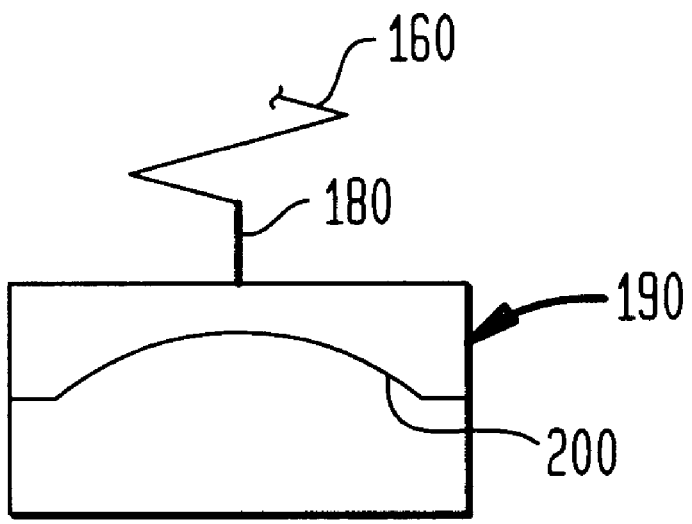
FIG. 4 is a plain view of a safety disk component with its membrane in a low volume position.
Figure 5:
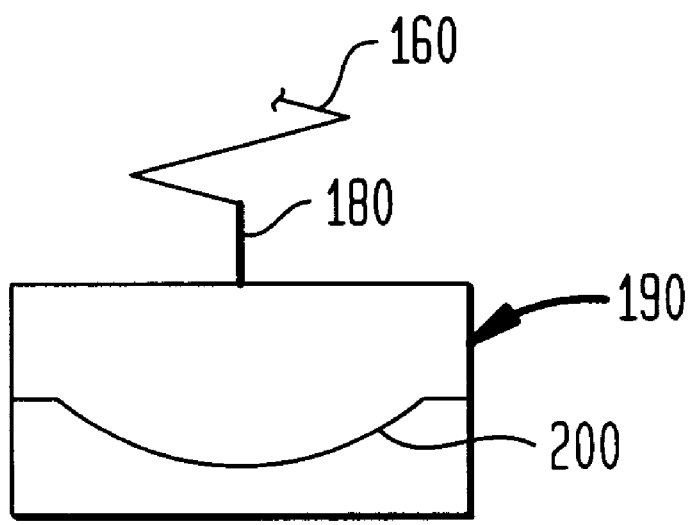
FIG. 5 is a plain view of a safety disk component with its membrane in a high volume position.

FIGS. 4 and 5 illustrate the second end 180 of the water vapor extraction element 160 terminating in the safety disk 190 component. The safety disk 190 comprises a membrane 200 which moves back and forth from the position illustrated in FIG. 4 to the position illustrated in FIG. 5 in response to changes in shuttle gas pressure in the water vapor extraction element 160.

Inflation of the tidal balloon 190, or in the alternative, movement of the membrane 200 (FIGS. 4 and 5) allows the shuttle gas to flow from the catheter 100 into the water vapor extraction element 160. During this transit, water vapor is extracted by the water vapor extraction element 160. The water vapor passes through the water vapor extraction element 160 and flows into the sump 90. Restricted check valve 210 allows the shuttle gas to flow into the cold trap 30. Check valve 135 allows for flow of shuttle gas out of the cold trap 30 and out of the tidal balloon 190. Note that the use of the tidal balloon 190 (FIG. 3) or the safety disk 190 (FIGS. 4 and 5)is not absolutely necessary as the sump 90 itself acts as a tidal volume. However, the use of a tidal volume having flexible walls is preferred.

If the quality of the vacuum created in the cold trap 30 is high, then liquid water will never form on the cold trap wall 40. Use of a vacuum system rather than relying on gravity to trickle down water condensed on the cold trap wall 40 has the advantage that it is insensitive to orientation. According to "*Efficiency and Temperature Dependance of Water Removal by Membrane Dryers,*" by Leckrone, et. al. Analytical Chemistry Vol. 69, Number 5, pages 911–918, the efficiency of Nafion's vapor removal process can be optimized by using a low flow rate through the Nafion tube 160. This is a consequence of the finite amount of time required to transport water through the Nafion's tubing walls. Accordingly, the invention includes the restricted check valve 210 on the third line 130. The restriction is designed to increase the "dwell" time of shuttle gas, i.e. to increase the amount of time the shuttle gas spends in the water vapor extraction element 160. The theory is that the slower the shuttle gas is traveling through the water vapor extraction element 160 the more time there is for it to dry. The restricted check valve 210 assures that the drying capacity of the water extraction element 160 is fully utilized.

As discussed above, the tidal balloon 190 inflates and deflates in response, to the pressure swings at the junction between the first line 100 and the third line 130. The balloon 190 is preferably sized to be a multiple of the volume of the water vapor extraction element 160. The balloon 190 may be biased to deflate either due to its own elasticity or due to the action of a spring. The balloon 190 may be biased by placing it in a vented chamber which constrains the full inflation volume of the balloon 190 to a designed value. Alternatively, a spring loaded rolling diaphragm air cylinder may be used instead of the tidal balloon 190 or the safety disk 190 (FIGS. 4 and 5).

In the event of an IAB perforation, the water vapor extraction element 160 and the tidal balloon 190 may be contaminated with blood. Due to its simple configuration, these components can be replaced as an assembly. Alternatively, in the embodiments in which the water vapor extraction element 160 is not in series with the catheter 100, and thus, have low flow rates through said water vapor extraction element 160, a filter may be placed in series with the assembly to protect it from blood contamination. The filter may include an integral restriction.

Figure 6:
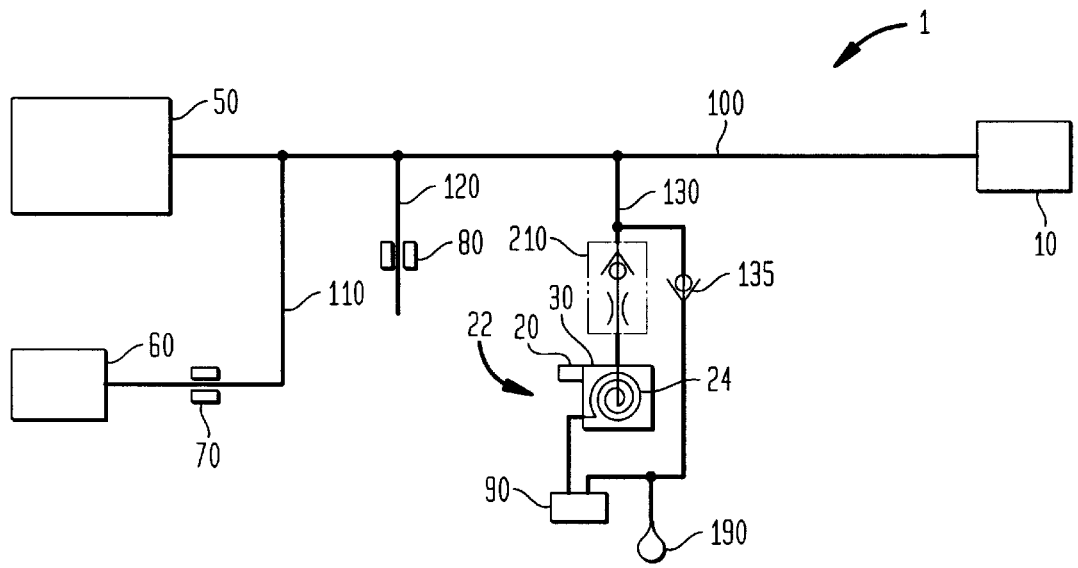
FIG. 6 is a block diagram of a second alternate embodiment of the intra-aortic balloon pump system with an improved condensation prevention system.

FIG. 6 illustrates a block diagram of another embodiment of the improved IABP system 1 having a water vapor extraction system 22 comprising a sump 90, a cooler 20, a cold trap 30, a tidal balloon 190, and a water vapor condensing coil section 24. The coil section 24 replaces the water vapor extraction element 160 as utilized in the embodiment illustrated in FIG. 3. The cold trap 30 may be filled with a fluid, or gel, or other appropriate conductive means to facilitate heat transfer between the coil section 24 and the cooler 20. Note that it is anticipated that the coil section 24 may be replaced with a section having another geometry. Possible alternative elements discussed for the other embodiments are equally applicable for this and all other embodiments of the invention.

As shuttle gas is shuttled from the pump 50 to the IAB 10 some shuttle gas flows into the third line 130, passes through restricted check valve 210 and into the coiled section 24. The cooled coiled section 24 behaves as a water vapor condensing element and causes at least some of the water vapor in the shuttle gas shuttle gas to condense. Water droplets are forced towards the sump by the intermittent flow of shuttle gas form the catheter 100. An inner surface of the coiled section 24 may be coated with a hydrophilic coating so as to facilitate the migration of condensed water droplets to the sump 90.

As shuttle gas is shuttled back from the IAB 10 to the pump 50, any shuttle gas lingering between restricted check valve 210 and check valve 135 is forced toward valve 135 and the pump 50. This one-way flow allows for the steady migration of condensed water droplets in the coiled section 24 to the sump 90.

Figure 7:
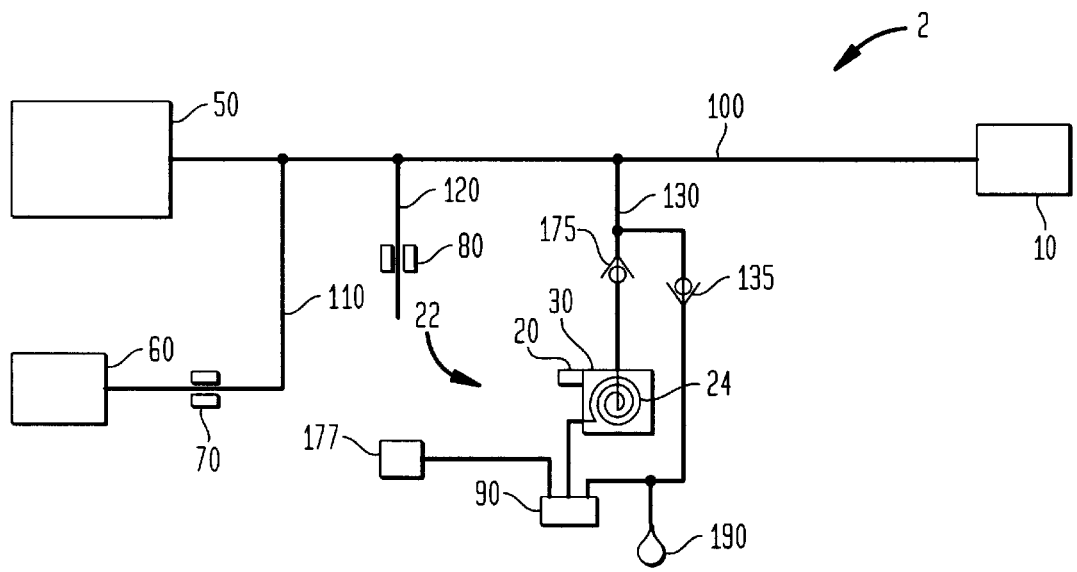
FIG. 7 is a block diagram of a third alternate embodiment of the intra-aortic balloon pump system with an improved condensation prevention system.

In an alternate embodiment of the invention, illustrated in FIG. 7, the restricted check valve 210 is replaced with an ordinary non-restricted check valve 175 and a second pump 177 is connected to the sump 90. As the pump 50 deflates the IAB 10 the second pump 177 may apply a front load pressure so as to restrict the entrance of shuttle gas through check valve 175. The front load pressure created by the second pump 177 accomplishes the same task as the restriction on the restricted check valve 210 (FIG. 3), namely, to increase the "lingering" time of the shuttle gas in the coiled section 24.

What is claimed is:

1. A method for operating an intra-aortic balloon pump system comprising
    a balloon pump, an intra-aortic balloon catheter connected to said pump and terminating in a balloon membrane, a water vapor removal system, and a valve system connected between the water vapor removal system and the intra-aortic balloon catheter,
    said water vapor removal system comprising a perfluorosulfonate ionomer tube communicating with the intra-aortic balloon catheter, said intra-aortic balloon Pump containing a predetermined amount of shuttle gas for inflation and deflation of the balloon membrane,
    comprising the steps of:
    (a) pumping a predetermined amount of a shuttle gas through the intra-aortic balloon catheter;
    (b) opening the valve system so as to allow the shuttle gas to pass into the perfluorosulfonate ionomer tube;
    (c) inflating the balloon membrane;
    (d) pumping said predetermined amount of shuttle gas in the opposite direction as in step (a);
    (c) closing the valve system for a predetermined amount of time so as to trap a predetermined amount of shuttle gas in the perfluorosulfonate ionomer tube;
    (d) deflating the balloon membrane;
    (e) repeating steps (a) through (d).

2. The method as claimed in claim 1 wherein the water vapor removal system further comprises an expansion means connected to one end of the perfluorosulfonate ionomer tube and wherein the valve system is kept open for a predetermined amount of time sufficient to allow the shuttle gas to enter both the perfluorosulfonate ionomer tube and the expansion means.

3. The method as claimed in claim 2 wherein the expansion means comprises a balloon.

4. The method as claimed in claim 2 wherein the expansion means comprises a safety disk.

5. The method as claimed in claim 1 wherein the valve system comprises a check valve and a restricted check valve in shunt connected between the perfluorosulfonate ionomer tube and the intra-aortic balloon catheter.

6. The method as claimed in claim 1 wherein the water vapor removal system further comprises a housing surrounding the perfluorosulfonate ionomer tube which communicates with a vacuum supply and further comprising the step of applying the vacuum to the housing so as to reduce the pressure in said housing.

7. The method as claimed in claim 1 wherein the water vapor removal system further comprises a housing surrounding the perfluorosulfonate ionomer tube and further comprising the step of purging an interior of said housing with a purge gas which is drier than the shuttle gas.

8. The method as claimed in claim 6 or 7 further comprising the step of cooling the housing.

9. A method for operating an intra-aortic balloon pump system comprising
    a balloon pump, an intra-aortic balloon catheter connected to said pump and terminating in a balloon membrane, a water vapor removal system, and a valve system connected between the water vapor removal system and the intra-aortic balloon catheter,
    said water vapor removal system comprising a perfluorosulfonate ionomer tube communicating with the intra-aortic balloon catheter, said intra-aortic balloon pump containing a predetermined amount of shuttle gas for inflation and deflation of the balloon membrane,
    comprising the steps of:
    (a) opening the valve system so as to allow the shuttle gas to pass into the perfluorosulfonate ionomer tube;
    (b) inflating the balloon membrane by pumping a predetermined amount of a shuttle gas through the intra-aortic balloon catheter;
    (c) closing the valve system for a predetermined amount of time so as to trap a predetermined amount of shuttle gas in the perfluorosulfonate ionomer tube;
    (d) deflating the balloon membrane by pumping said predetermined amount of shuttle gas in the opposite direction as in step (a);
    (e) repeating steps (a) through (d).

10. A method for operating an intra-aortic balloon pump system comprising
    a balloon pump, an intra-aortic balloon catheter connected to said pump and terminating in a balloon membrane, a water vapor removal system, and a valve system connected between the water vapor removal system and the intra-aortic balloon catheter,
    said water vapor removal system comprising a perfluorosulfonate ionomer tube communicating with the intra-aortic balloon catheter, said intra-aortic balloon pump containing a predetermined amount of shuttle gas for inflation and deflation of the balloon membrane,
    said valve system comprising a first one-way valve and a second one-way valve in shunt connected between the perfluorosulfonate ionomer tube and the intra-aortic balloon catheter, comprising the steps of:

(a) opening the first one-way valve and inflating the balloon membrane by pumping a predetermined amount of a shuttle gas through the intra-aortic balloon catheter;

(b) closing the first one way valve, opening at least partially the second one-way valve, and deflating the balloon membrane by pumping said predetermined amount of shuttle gas in the opposite direction as in step (a);

(c) repeating steps (a) through (b).

* * * * *